(12) United States Patent
Farhadi

(10) Patent No.: US 9,867,529 B2
(45) Date of Patent: Jan. 16, 2018

(54) ENDOSCOPE ACCESSORY

(75) Inventor: Ashkan Farhadi, Burr Ridge, IL (US)

(73) Assignee: IZOSCOPE INC, Irvine, CA (US)

( * ) Notice: Subject to any disclaimer, the term of this patent is extended or adjusted under 35 U.S.C. 154(b) by 44 days.

(21) Appl. No.: 12/266,953

(22) Filed: Nov. 7, 2008

(65) Prior Publication Data

US 2010/0121144 A1    May 13, 2010

(51) Int. Cl.
| | |
|---|---|
| *A61B 1/00* | (2006.01) |
| *A61B 1/273* | (2006.01) |
| *A61B 8/12* | (2006.01) |
| *A61B 1/04* | (2006.01) |
| *A61B 1/005* | (2006.01) |
| *A61M 25/10* | (2013.01) |

(52) U.S. Cl.
CPC ........ *A61B 1/2736* (2013.01); *A61B 1/00082* (2013.01); *A61B 1/00135* (2013.01); *A61B 8/12* (2013.01); *A61B 1/005* (2013.01); *A61M 25/1011* (2013.01); *A61M 2025/1052* (2013.01)

(58) Field of Classification Search
CPC ..... A61B 1/00082; A61B 1/018; A61B 1/267; A61B 1/2673; A61B 1/2676; A61B 1/00135; A61B 1/005; A61B 8/12
USPC ........ 600/104, 113–116, 140, 153, 154, 194, 600/121–125; 604/96.01, 101.01–101.05
See application file for complete search history.

(56) References Cited

U.S. PATENT DOCUMENTS

| | | |
|---|---|---|
| 3,417,744 A | 12/1968 | Mishkin |
| 3,449,037 A | 6/1969 | Koester |

(Continued)

FOREIGN PATENT DOCUMENTS

| | | | |
|---|---|---|---|
| AU | 651843 B2 | 8/1994 | |
| IL | WO2007/017854 | * 2/2007 | ................ 600/106 |

(Continued)

OTHER PUBLICATIONS

Alvarado et al., "Microbiologic assessment of disposable sterile endoscopic sheaths to replace high-level disinfection in reprocessing: A prospective clinical trial with nasopharygoscopes." American journal of infection control 37.5 (2009): 408-413.

(Continued)

*Primary Examiner* — Timothy J Neal
(74) *Attorney, Agent, or Firm* — Kader Gacem; Jerisat Law Firm

(57) ABSTRACT

This invention relates generally to an endoscope accessory. This device uses an overtube with an inflatable positioning balloon that can be inflated after placement of the overtube just proximal to the tip of the endoscope or echoendoscope. This balloon creates a temporary blockade of the gastrointestinal tract proximal to the portion that needs to be examined. The other part of the device is a catheter with an occlusion balloon affixed to its free endportion and can be passed through a passageway within the overtube and extended beyond the tip of the endoscope, distal to the part of the gastrointestinal tract that needs to be examined. Inflation of this balloon together with positioning balloon creates a closed space within the body cavity that can be filled with air or water for improving the quality of the examination with regular endoscope of echoendoscope, respectively, while reducing the examination complications.

18 Claims, 6 Drawing Sheets

(56) References Cited

U.S. PATENT DOCUMENTS

| | | | |
|---|---|---|---|
| 3,805,770 A | 4/1974 | Okada | |
| 4,198,981 A | 4/1980 | Sinnreich | |
| 4,445,892 A | 5/1984 | Hussein | |
| 4,453,545 A * | 6/1984 | Inoue | 604/101.05 |
| 4,646,722 A | 3/1987 | Silverstein et al. | |
| 4,696,668 A | 9/1987 | Wilcox | |
| 4,809,678 A | 3/1989 | Klein | |
| 4,886,049 A | 12/1989 | Darras | |
| 5,105,819 A | 4/1992 | Wollschlager et al. | |
| 5,159,919 A | 11/1992 | Chikama | |
| 5,198,894 A | 3/1993 | Hicks | |
| 5,210,814 A * | 5/1993 | McNally | G02B 6/06 385/116 |
| 5,217,001 A | 6/1993 | Nakao et al. | |
| 5,441,503 A * | 8/1995 | Considine | A61B 18/14 600/158 |
| 5,458,132 A | 10/1995 | Yabe et al. | |
| 5,483,951 A * | 1/1996 | Frassica et al. | 600/104 |
| 5,496,259 A | 3/1996 | Perkins | |
| 5,554,098 A | 9/1996 | Yabe et al. | |
| 5,569,159 A | 10/1996 | Anderson et al. | |
| 5,569,161 A | 10/1996 | Ebling et al. | |
| 5,575,756 A * | 11/1996 | Karasawa | A61B 1/00068 600/121 |
| 5,630,782 A | 5/1997 | Adair | |
| 5,702,344 A | 12/1997 | Silverstein | |
| 5,733,242 A | 3/1998 | Rayburn et al. | |
| 5,779,624 A * | 7/1998 | Chang | 600/114 |
| 5,863,286 A | 1/1999 | Yabe et al. | |
| 5,904,648 A * | 5/1999 | Arndt et al. | 600/120 |
| 5,916,145 A * | 6/1999 | Chu et al. | 600/121 |
| 5,924,977 A | 7/1999 | Yabe et al. | |
| 6,004,273 A | 12/1999 | Sakamoto | |
| 6,149,581 A | 11/2000 | Klingenstein | |
| 6,234,958 B1 * | 5/2001 | Snoke | A61B 1/00082 600/106 |
| 6,293,909 B1 | 9/2001 | Chu et al. | |
| 6,440,061 B1 * | 8/2002 | Wenner | A61B 1/3132 600/114 |
| 6,530,881 B1 | 3/2003 | Ailinger et al. | |
| 6,749,601 B2 | 6/2004 | Chin | |
| 6,793,621 B2 | 9/2004 | Butler et al. | |
| 6,830,545 B2 | 12/2004 | Bendall | |
| 6,852,077 B2 | 2/2005 | Ouchi et al. | |
| 6,852,078 B2 | 2/2005 | Ouchi | |
| 6,869,393 B2 | 3/2005 | Butler | |
| 6,908,428 B2 | 6/2005 | Aizenfeld et al. | |
| 7,052,456 B2 * | 5/2006 | Simon | 600/120 |
| 7,695,428 B2 | 4/2010 | Machida | |
| 7,905,830 B2 | 3/2011 | Stefanchik et al. | |
| 8,262,561 B2 | 9/2012 | Kress | |
| 8,465,419 B2 | 6/2013 | Moriyama | |
| 8,647,261 B2 | 2/2014 | Jaworek et al. | |
| 2001/0049509 A1 * | 12/2001 | Sekine et al. | 600/104 |
| 2002/0077527 A1 * | 6/2002 | Aydelotte | 600/120 |
| 2002/0185135 A1 * | 12/2002 | Amar | 604/96.01 |
| 2003/0172941 A1 | 9/2003 | Streifinger et al. | |
| 2003/0229269 A1 | 12/2003 | Humphrey | |
| 2004/0143161 A1 | 7/2004 | Baror et al. | |
| 2005/0107664 A1 * | 5/2005 | Kalloo et al. | 600/115 |
| 2005/0124856 A1 | 6/2005 | Fujikura | |
| 2005/0137457 A1 | 6/2005 | Machida | |
| 2005/0165273 A1 | 7/2005 | Takano | |
| 2005/0215855 A1 | 9/2005 | Machida | |
| 2006/0020165 A1 * | 1/2006 | Adams | A61B 1/00094 600/121 |
| 2006/0074274 A1 * | 4/2006 | Friedman et al. | 600/114 |
| 2006/0111611 A1 | 5/2006 | Eizenfeld et al. | |
| 2007/0010785 A1 | 1/2007 | Sekiguchi | |
| 2007/0038109 A1 | 2/2007 | Nierich | |
| 2007/0049797 A1 | 3/2007 | Yoshida | |
| 2007/0066869 A1 | 3/2007 | Hoffman | |
| 2007/0260117 A1 | 11/2007 | Zwolinski et al. | |
| 2007/0299308 A1 | 12/2007 | Fujikura | |
| 2008/0171989 A1 * | 7/2008 | Bell | A61M 25/0662 604/170.02 |
| 2009/0227835 A1 * | 9/2009 | Terliuc | 600/106 |
| 2010/0010308 A1 | 1/2010 | Braun et al. | |
| 2012/0010468 A1 | 1/2012 | Afridi | |
| 2012/0283663 A1 | 11/2012 | Delegge | |
| 2014/0150782 A1 | 6/2014 | Vazales et al. | |

FOREIGN PATENT DOCUMENTS

| | | | |
|---|---|---|---|
| WO | WO-97/04828 A1 | 2/1997 | |
| WO | WO-01-00080 A2 | 1/2001 | |
| WO | WO-2004-008950 A1 | 1/2004 | |
| WO | WO-2005-110185 A1 | 11/2005 | |
| WO | WO2007017854 * | 2/2007 | H05B 37/00 |
| WO | WO-2014-092650 A1 | 6/2014 | |

OTHER PUBLICATIONS

Baker et al., "Evaluation of endoscope sheaths as viral barriers." The Laryngoscope 109.4 (1999): 636-639.

Kovaleva et al., "Is bacteriologic surveillance in endoscope reprocessing stringent enough?." Endoscopy 41.10 (2009): 913.

Noronha et al., "A 21st century nosocomial issue with endoscopes." BMJ: British Medical Journal 348 (2013).

Pajkos et al., "Is biofilm accumulation on endoscope tubing a contributor to the failure of cleaning and decontamination?." Journal of Hospital Infection 58.3 (2004): 224-229.

* cited by examiner

ENDOSCOPE ACCESSORY

FIELD OF INVENTION

This invention relates generally to an accessory for endoscopic examination of body organs particularly gastrointestinal tract. More particularly, the invention relates to creation of a closed region around the tip of an endoscope introduced into a visceral organ.

BACKGROUND OF INVENTION

An endoscope is a well-known optical system for evaluation of internal organs that was disclosed and claimed in U.S. Pat. No. 3,449,037 to C. J. Koester. Currently used fiberoptic endoscopes are comprised of many lenses mounted in a flexible tube to relay an image from inside a body cavity for viewing by a physicians for diagnosis or manipulation inside those cavitary spaces. Endoscopic ultrasound (EUS) is a device that combines endoscope and ultrasound to image the gastrointetinal wall and surrounding structures. The first prototype for human use was developed in 1980, and several generations of echoendoscopes have been developed since then. In the 1990 the capability of obtaining tissue samples by this method resulted in further applications of this test to sample internal structures and organs. The ultrsound tranducer is positioned at the tip of endoscope and the key components of the transducer are the piezoelectric crystals that vibrate to produce ultrasonic waves. The ultrasounic waves then travel through gastrointestinal lumen to its wall and beyond the visceral wall into the surrounding organs and the reflection of these ultrasound waves will be detected by the same crystals at the transducer and reconstruction of these reflections will result in creating a real time image of the gastrointestinal wall and its sourounding structures. The ultrasonic wave reflects from the surface of structures different density and can pass very well through fluid containg and solid structures. However, air create a barrier to ultrasonic was passage and hampers obtaing ultrasonic images. Thus many attempts have been done to minimize the amount of interfering air between the transducer and the examining structure. These efforts could be seen in early patents Yokoi in 1988 (Ultrasonic endoscope, U.S. Pat. No. 4,779,624), Wollschlager in 1992 (Ultrasound endoscope device, U.S. Pat. No. 5,105,819), Sakamoto in 1994(Ultrasound transmission medium feed device for endoscopically inserting ultrasound probe, U.S. Pat. No. 6,004,273) and recently in the patent application by Nierich in 2007 (Transmission device for ultrasonic imaging system, publication No 2007/0038109). In all of these, there is balloon a the end of the endoscope encloses the transducer and will be filled With water permit acoustic coupling between the transducer and the luminal wall or other gastrointestinal structures. This is particularly helpful in the part of gastrointestinal tract where the diameter of the lumen is small and the inflatted balloon makes a good circumferential contact with the intestinal wall and thus creates a good acoustic coupling. In most parts of the gastrointnal tract, however, the large diameter of the lumen and or the angle of the transducer in relation to the intestinal wall result in an inadequate contact between the transducer balloon and the intestinal wall and thus, the operator usually use water infusion to fill the portion of the gastrointestinal tract with water and create acoustic coupling between the transducer and the examinimed structures. Unfortunately, the gastrointestinal tract is not a closed region and the infused water soon moves to other portion of the gastrointestinal tract and this can often result in poor image quality despite repeated infusion of water around the transducer. In addition, infusion of significant amount of water during the examination could result in untoward problems such as aspiration of the water into the patient's airway or overdistention of the gastrointestinal tract. To overcome this problem I devised a device that creates a closed space around the ultrasound transducer using two balloons. Using two balloons in the gastrointestinal system has been suggested for the first time by Wilcox in 1987(Double balloon nasobiliary occlusion catheter for treating gallstons and method of using the same U.S. Pat. No. 4,696,668) who useds a double balloon catheter to make a closed space inside the bile duct to direct the chemicals used for lysing of gall bladder stone into the gall bladder and limit the exposure of the rest of the biliary system with this toxic agent. Later a two balloon approach was used on various endoscopic devices for assisting the movement of the endoscope deep down into the small intestine. The initial devices was proposed by Fujikura in 2005(Insertion assisting tool for endoscope, publication No 2005/0124856), Takakano in 2005 (Endoscope apparatus, publication No 2005/0165273), Machida in 2005 (Endoscope apparatus, publication No 2005/0215855), and Yoshida in 2007 Double-balloon endoscope system, publication No 2007/0049797). In all these patents an over tube with a balloon is used to secure the position of the endoscope inside the gastrointestinal tract and the second balloon on the inserting tip of the endoscope is used to anchor and move the endoscope forward using alternating inflating and deflating of these two balloons. In the current invention, on the other hand the structure of the balloons and their functions are different.

SUMMARY OF THE INVENTION

This device presented in this invention enhances capabilities of an endoscope in maintaining luminal view and is comprised of an overtube with an inflatable, freely moveable positioning balloon at its distal endportion. The overtube can slide over an endoscope inside the body cavity, and its distal tip is placed just proximal to the distal tip of endoscope, proximal to the portion of the gastrointestinal tract that needs to be examined. At this place the positioning balloon is inflated to secure the position of the overtube. The other part of the device is a catheter with an occlusion balloon at its distal endportion that can be passed through a passageway provided along the overtube and extends beyond the tip of the endoscope distal to the portion of the gastrointestinal tract that needs to be examined. At this position, the occlusion balloon is inflated. This creates a closed space between the two inflated balloon in the gastrointestinal tract at the portion of the gastrointestinal tract that needs to be examined. This closed space can be inflated with air for detailed examination and treatment of the area with a regular endoscope, or filled with water for acoustic coupling between the endoscope transducer and gastrointestinal structures for examination with an echoendoscope. The inflated balloons prevent escape of air or water from the examination site. This improves the acoustic coupling and provides for better examination in a larger region of the gastrointestinal tract that needs to be examined. This reduces unnecessary overinflation of the other portion of the gastrointestinal tract with air and water, and in the case of water, reduces the risk such as water toxicity or aspiration. Throughout the procedure, the pressure of the water or air in the closed space is monitored to prevent overdistention of the region with water or air. After termination of the examination, the water or air is suctioned out of the part of the gastrointestinal tract examined.

In a preferred embodiment, and endoscope accessory embodying the present invention include a flexible overtube, an inflatable positioning balloon, a cuff carried by the overtube, a fluid conduit, a catheter tube, and a catheter situated in the catheter tube and terminating in an inflatable occlusion balloon. The overtubedefines a passageway for receiving the shaft of an endoscope which can be a conventional endoscope of and echoendoscope. The cuff is affixed to the overtube at the proximal endportion thereof. The inflatable positioning balloon is affixed to the overtube at the distal endportion thereof. The fluid conduit defines an inflation as well as evacuation or suction passageway for fluid or air removal from the gastrointestinal tractregion subject to examination. The midportion of the catheter is situated in and carried by the overtube, which the distal endportion of the catheter carrying the inflatable occlusion balloon, is freely positionable within the gastrointestinal tract at the predetermined location.

BRIEF DESCRIPTION

DETAILED DESCRIPTION OF THE INVENTION

Figure 1:
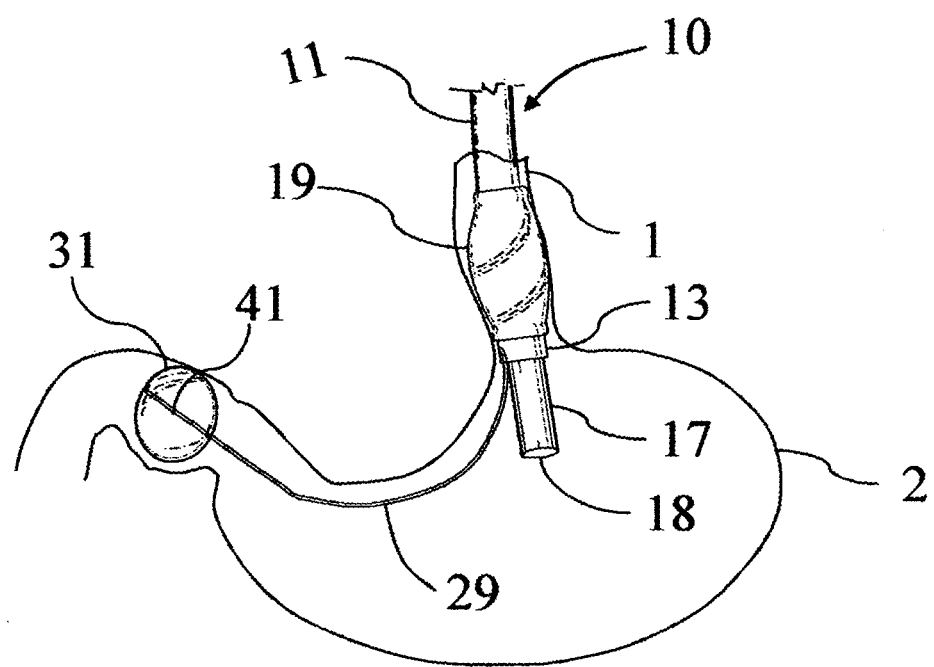
FIG. 1 is a schematic representation showing positioning of the endoscope accessory in use.
Figure 2:
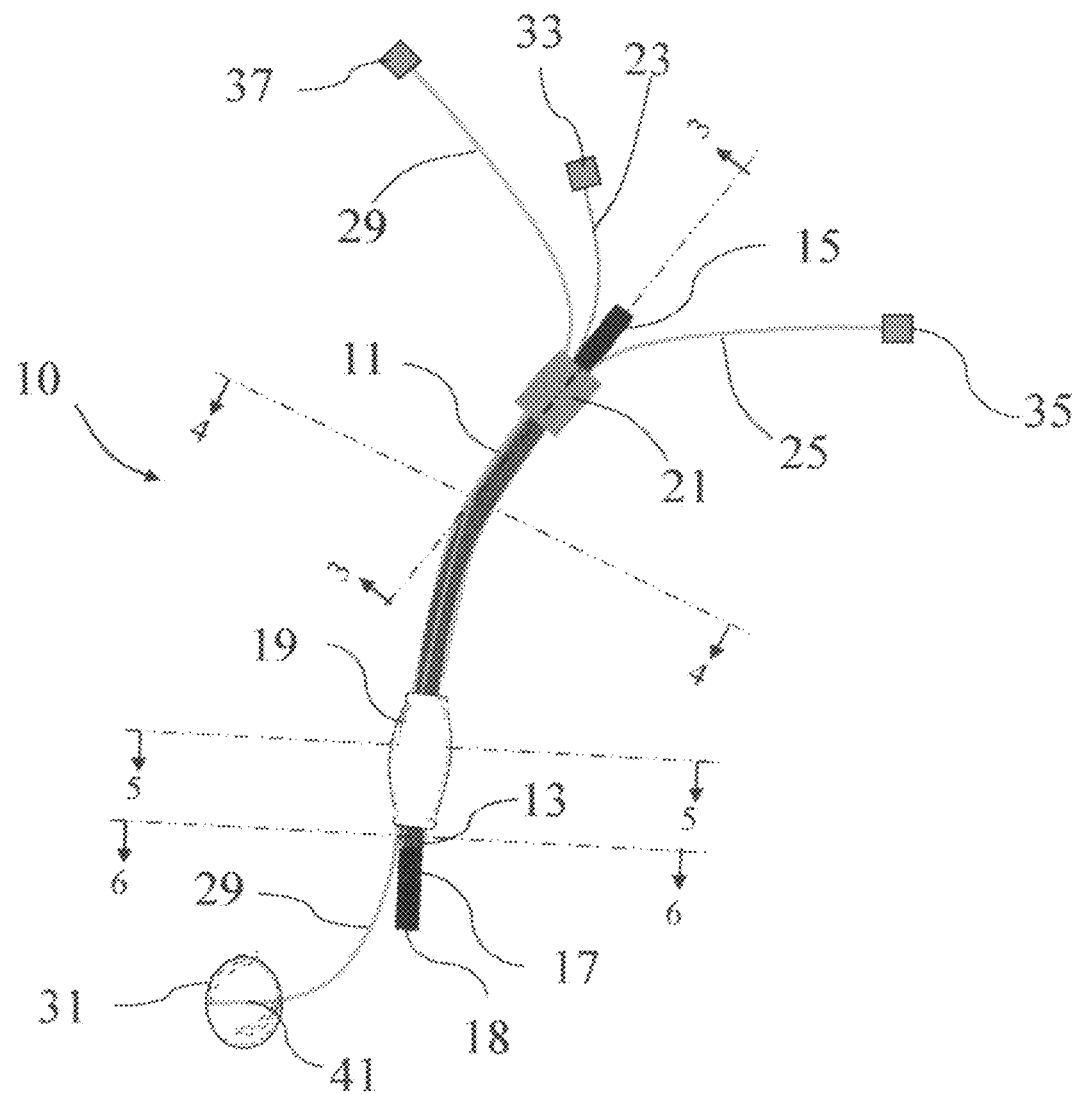
FIG. 2 is an overall plan view of the present invention.
Figure 3:
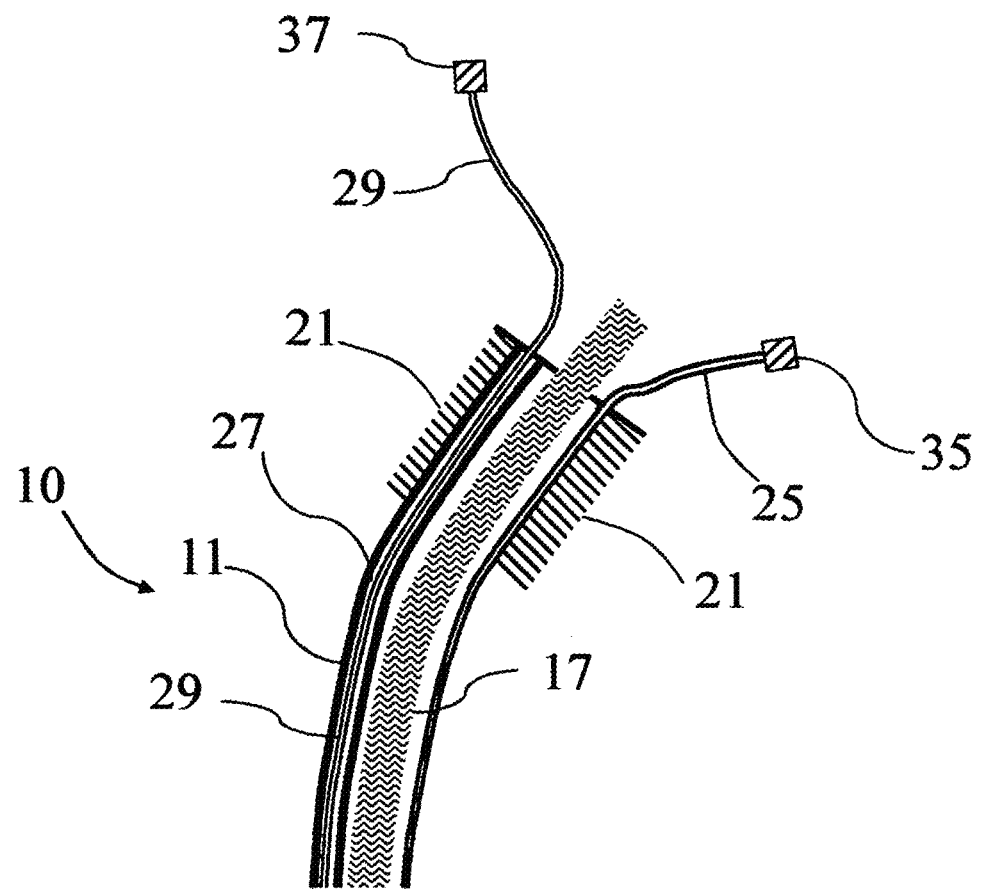
FIG. 3 is a longitudinal sectional view of the device shown in FIG. 2 take along plane 3-3.
Figure 4:
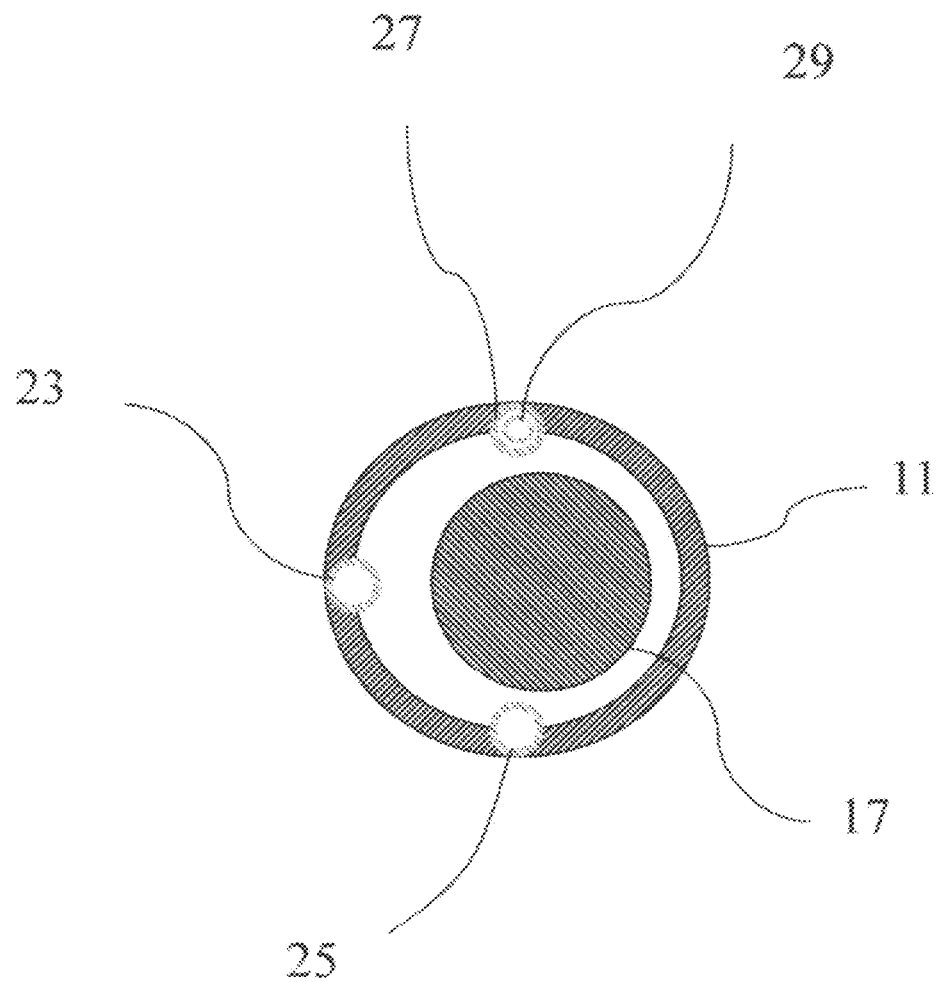
FIG. 4 is a sectional view of the device shown in FIG. 2 take along plane 4-4.
Figure 5:
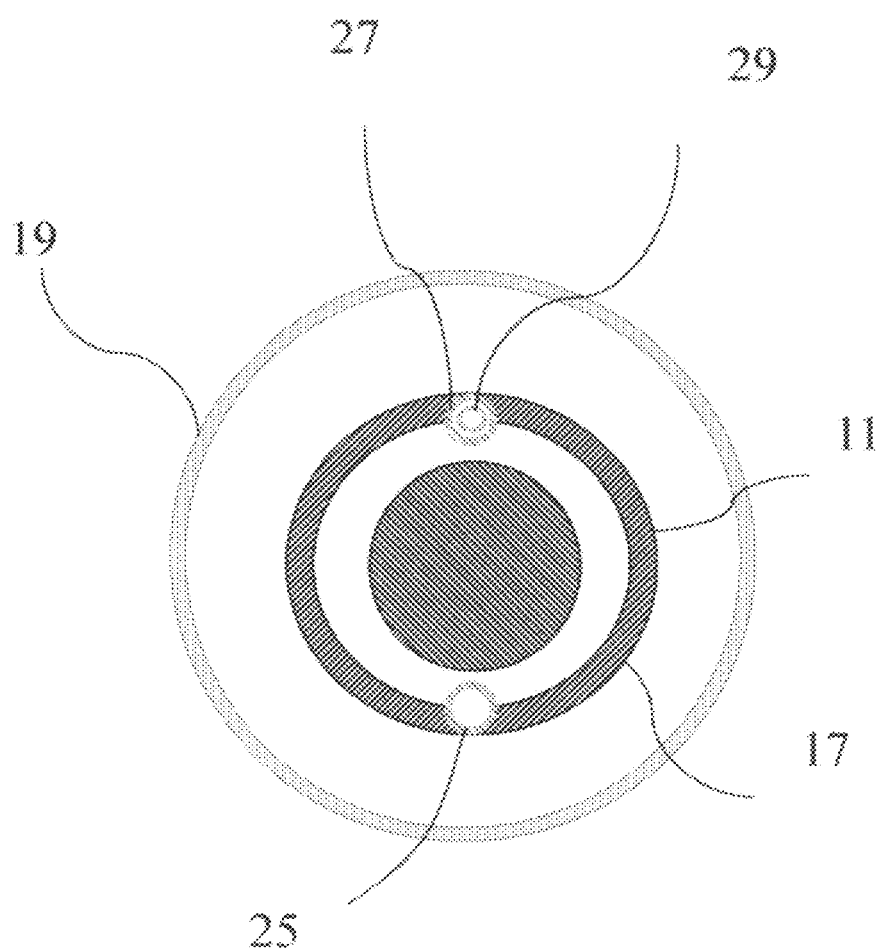
FIG. 5 is a sectional view of the device shown in FIG. 2 take along plane 5-5.

Double Balloon Endoscope Overtube 10 is made up of these components:

A—Overtube: As it is depicted in FIGS. 1 and 2, the Double Balloon Endoscope Overtube 10 is composed of a flexible tube 11 preferably transparent, that can be removably placed over a regular endoscope or echoendoscope shaft 17 and inserted inside a human gastrointestinal tract. The overtube has a proximal endportion 15 and a distal endportion 13. The overtube distal endportion 13 is inserted into the human gastrointestinal tract and an inflatable positioning balloon 19 is affixed to this area to secure the position of the overtube inside the body cavity. The overtube proximal endportion 15 stays out of the human body, and a cuff 21 is affixed to this portion to facilitate grasping and manipulation of the overtube 11 for insertion and positioning inside the body cavity by the endoscopist. The diameter of the overtube 11 is large enough to freeely receive a regular endoscope or echoendoscope shaft 17 therewithin. The length of the overtube 11 is large enough to cover about half of the length of a regular endoscope or echoendoscope shaft 17. This provides enough room for placement of the endoscope or echoendoscope shaft 17 into the body cavity first and use the shaft 17 as the guide to slide the overtube 11 over the endoscope shaft 17 inside the body cavity. The other structures of the overtube include:

1. An inflation tube 23 carried by the overtube 11 that is used to inflate the positioning balloon 19 at the end of the overtube. There is an inflation tube connection 33 at the proximal end of the inflation tube 23 that can be used to connect the inflation tube 23 to a syringe or a pump for inflating the positioning balloon 19.

2. Fluid conduit 25 is carried by the overtube 11 and used to infuse or empty the water or air inside the body cavity at the region of the gastrointestinal tract that needs to be examined. There is a fluid conduit connection 26 at the proximal end of the conduit 25 that can be used to connect conduit to pump or suction for infusion or suctioning of watch or air inside the body cavity, respectively.

3. Catheter tube 27 carried by the overtube 11 and is used as a passageway for the catheter and its occlusion balloon.

Figure 6:
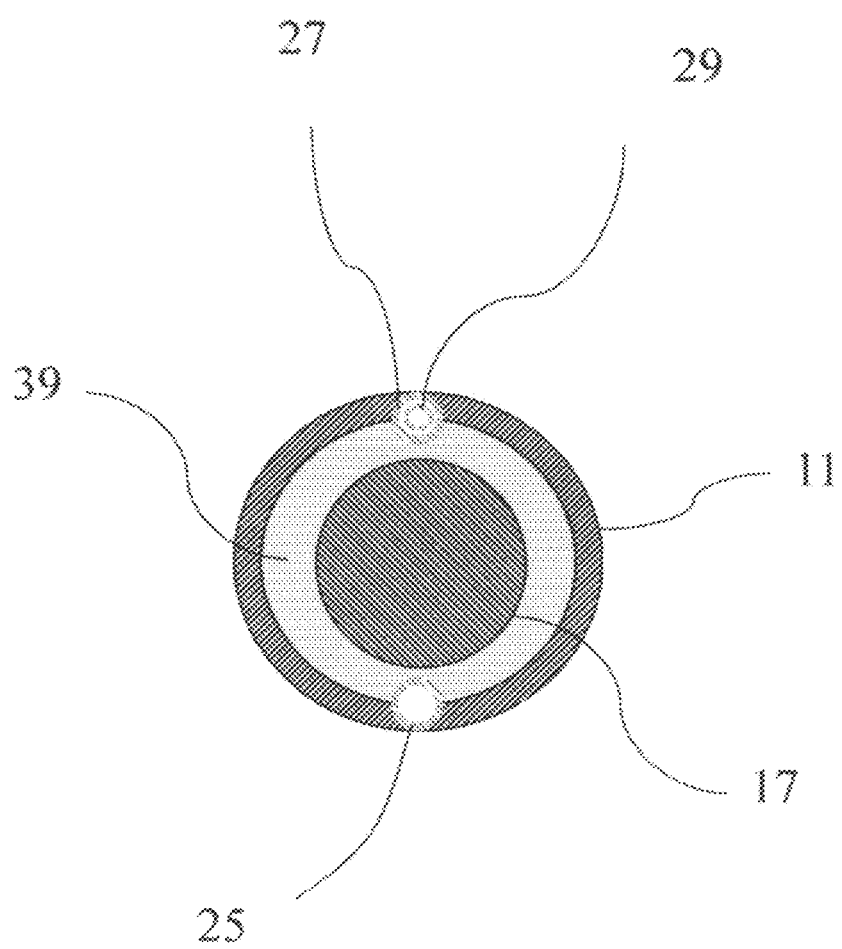
FIG. 6 is a sectional view of the device shown in FIG. 2 take along plane 6-6.

4. Optional washer 39 (FIG. 6) at the distal endportion of the overtube 11 is made of a soft material and creates a cushion within the lumen of the overtube 11 and fill the space between the shaft of the endoscope or echoendoscope 17 and the overtube to form a fluid tight seal so as to prevent leakage of air or water between these two structure. This washer is located within the lumen of the overtube 11 at the distal endportion 13 and permits free sliding movement of the shaft of the endoscope of echoendoscope 17 within the lumen of the overtube 11. Alternatively, the flexible overtube can be constricted at the distal endportion to provide the desired fluid tight seal.

B—catheter and Occlusion balloon: As it is depicted in FIGS. 1 and 2, the catheter 29 is a flexible hollow tube that can be passed through the catheter tube 27 along the overtube 11. This catheter 29 has a distal free endportion 41 that can be independantly positioned distal to the part of the gastrointestinal tract that needs to be examined. An inflatable occlusion balloon 31 is affixed to distal free endportion 41 of the catheter 29. A catheter tube connection 37 at the proximal end of the catheter tube 29 that can be used to connect the catheter tube 29 to a syringe or a pump for inflating the occlusion balloon 31.

In use, before the insertion of the endoscope or echoendoscope shaft 17 into the patient's body cavity, the overtube 11 is passed over the endoscope or echoendoscope shaft 17 and is kept at the proximal end of the shaft close to the endoscope knob area. This leaves the distal half of the endoscope or echoendoscope shaft 17 to easily intube the body cavity. When the body cavity is intubated by the endoscope or echoendoscope and the distal portion of the endoscope or echoendoscope shaft in within the body cavity, the overtube 11 is glided over the endoscope or echoendoscope shaft 17 into the body cavity and advanced so that the overtube distal portion 13 gets close to the endoscope or echoendoscope tip 18. At this point the positioning balloon 19 at the overtube distal portion 13 is inflated to secure the position of the overtube 11 and create transient blockage of passage of air or water proximal to the inflated positioning balloon 19. Then the catheter 29 and occlusion balloon 31 at its free endportion 41 is inserted into the catheter tube 27 and passed along into the body cavity. After situating the catheter free endportion 41 at the desired location, the occlusion balloon is inflated to create transient blockage of passage of air or water. This creates a closed region around the tip of endoscope or echoendoscope 18 in the gastrointestinal tract portion that needs to be examined. This region can be filled with air for examination with regular endoscope or with water for examination with echoendoscope. The water or air is introduced into or removed from this closed region using fluid conduit 25. The pressure inside this close area is continuously measured, and can be adjusted by infusion or suction through conduit 25.

After completion of the examination, the air or water inside the closed region of the gastrointestinal tract is suctioned out via fluid conduit 25. After complete evacuation of air or water, the positioning balloon 19 and the occlusion balloon 31 are deflated, and the overtube 11 removed independent of the endoscope or echoendoscope shaft 11, or together with the endoscope or echoendoscope shaft 11, as convenient.

The invention claimed is:

1. An endoscopic device comprising:
   at least one endoscope overtube for diagnostic and therapeutic intervention, the overtube including an inner surface and an outer surface, a through lumen, a proximal end portion, and a distal end portion, and an overtube passageway, and at least one positioning balloon, which is affixed at the distal end portion of the overtube;
   at least one elongated catheter to be received by the at least one endoscope overtube, which includes at least one occlusion balloon extending out of the at least one elongated catheter at a free end portion of the at least one elongated catheter extending beyond the distal end portion of the endoscope overtube, the endoscope overtube being operatively connected to the at least one catheter;
   an endoscope receivable and positionable in the through lumen, wherein before an insertion of the endoscope in a gastrointestinal tract portion the at least one overtube is passed over a proximal end of the endoscope using the through lumen and the distal end portion of the at least one overtube is kept near the proximal end of the endoscope;
   at least one washer affixed to the through lumen at the distal end portion for forming a seal to prevent passage of fluids and gases between the at least one endoscope overtube and the endoscope and which permits free sliding movement of the at least one endoscope overtube over the endoscope; and
   a cuff carried the at least one endoscope overtube and affixed to the proximal end portion,
   wherein after the insertion of the endoscope into the gastrointestinal tract portion the at least one overtube is glided past the proximal end of the endoscope into the gastrointestinal tract portion and advanced so that the distal end portion gets close to a distal end of the endoscope,
   wherein inside the gastrointestinal tract portion the at least one endoscope overtube is operated between a first open position allowing passage of fluids and gases and a second closed position substantially blocking passage of fluids and gases through the gastrointestinal tract portion for diagnostic and therapeutic intervention,
   wherein after the diagnostic and therapeutic intervention the at least one endoscope overtube is configured to selectively allow removal of the at least one endoscope overtube from the gastrointestinal tract portion and backward from the proximal end of the endoscope before a removal of the endoscope from the gastrointestinal tract portion, and
   wherein the least one occlusion balloon is slidably moveable relative to the at least one endoscope overtube for selectively sealing a portion of the gastrointestinal tract portion for examination and therapeutic treatment.

2. The device of claim 1, wherein each of the at least one positioning balloon and the at least one occlusion balloon is moveable between a first deflated position allowing passage of fluids and gases and a second inflated position substantially blocking passage of fluids and gases independently of each other inside the gastrointestinal tract portion.

3. The device of claim 1, wherein when the at least one positioning balloon, and the at least one occlusion balloon are inflated then at least one closed region is formed around a tip of the at least one elongated catheter for examination of the gastrointestinal tract portion.

4. A diagnostic and therapeutic device, the device comprising:
   at least one elongated endoscope member, the at least one elongated endoscope member comprises an inner surface and an outside surface;
   at least one catheter receivable by the at least one elongated endoscope member;
   an endoscope having a proximal end and a distal end;
   at least one washer for forming a seal to prevent passage of fluids and gases through the at least one elongated member;
   a positioning balloon located on the outside surface adjacent to a distal end portion of the at least one elongated endoscope member; and
   a cuff carried by the at least one elongated endoscope member and affixed to a proximal end portion;
   wherein the at least one catheter includes an occlusion balloon at a distal end extending beyond the distal end portion of the at least one elongated endoscope member and operatively connected to the at least one elongated endoscope member to selectively restrict the flow of fluids and gases throughout a body portion,
   wherein after an insertion of the endoscope into a gastrointestinal tract portion the at least one endoscope member is glided over the proximal end of the endoscope through a lumen of the at least one endoscope member into the gastrointestinal tract portion and advanced so that the distal end portion gets close to the distal end of the endoscope,
   wherein after an diagnostic and therapeutic intervention the at least one elongated endoscope member is configured to be selectively removable from the gastrointestinal tract portion and backward from the proximal end of the endoscope before a removing of the endoscope from the gastrointestinal tract portion, and
   wherein the least one occlusion balloon is slidably moveable relative to the at least one elongated endoscope member for selectively sealing a portion of the gastrointestinal tract portion for examination and therapeutic treatment.

5. The device of claim 4, wherein the cuff is affixed to facilitate grasping and manipulation of the at least one elongated endoscope member for insertion and positioning inside a body cavity with the proximal end portion remaining outside the body cavity.

6. The device of claim 5, wherein the cuff is affixed to facilitate grasping and manipulation of the at least one elongated endoscope member for insertion and positioning inside a body cavity with the proximal end portion remaining outside the body cavity.

7. The device of claim 5, wherein the occlusion balloon substantially restricts the flow of gases and fluids away from and into the closed region of the gastrointestinal tract portion near the distal end of the at least one catheter.

8. The device of claim 5, wherein the positioning balloon is a freely moveable balloon.

9. The device of claim 4, wherein the plurality of balloons create at least one closed region throughout the inner surface of the at least one elongated member for allowing diagnostic and therapeutic intervention treatment.

10. An endoscopic device comprising:
at least one flexible elongated endoscope overtube for diagnostic and therapeutic intervention, the endoscope overtube including an inner surface and an outer surface, at least one washer for forming a seal to prevent passage of fluids and gases through the elongated overtube, a proximal end portion, a distal end portion, a through lumen, at least one positioning balloon located on the outer surface adjacent to the distal end portion of the at least one flexible elongated endoscope overtube;
an endoscope positionable in the through lumen, wherein before an insertion of the endoscope in a gastrointestinal tract portion the at least one endoscope overtube is passed over a proximal end of the endoscope using the through lumen of the at least one endoscope overtube and the distal end portion of the at least one endoscope overtube is kept near the proximal end of the endoscope;
at least one elongated catheter; and
a cuff carried by the at least one elongated overtube and affixed to the proximal end portion,
wherein after an insertion of the endoscope into a gastrointestinal tract portion the at least one endoscope overtube is glided past the proximal end of the endoscope into the gastrointestinal tract portion and advanced so that the distal end portion gets close to a distal end of the endoscope,
wherein inside the gastrointestinal tract portion the at least one endoscope overtube being operatively connected to the at least one elongated catheter,
wherein the at least one elongated catheter includes an occlusion balloon at a distal end to prevent escape of air or water from the gastrointestinal tract portion,
wherein after the diagnostic and therapeutic intervention the at least one endoscope overtube is removable from the gastrointestinal tract portion and backward from the proximal end of the endoscope before a removing of the endoscope from the gastrointestinal tract portion, and
wherein the least one occlusion balloon is slidably moveable relative to the at least one elongated endoscope member for selectively sealing a portion of the gastrointestinal tract portion for examination and therapeutic treatment.

11. An endoscope accessory comprising:
an endoscope overtube having a proximal end portion, a distal end portion, an outer surface, an inner surface, and an overtube passageway;
at least one positioning balloon associated with the endoscope overtube at the distal end portion;
an endoscope having a proximal end and a distal end;
a washer affixed to a through lumen of the endoscope overtube at the distal end portion for filling space between the inner surface and the endoscope forming a seal to prevent passage of fluids and gases through the overtube and which permits free sliding movement of the endoscope within the endoscope overtube;
a cuff affixed to the proximal end portion; and
a catheter including at least one positionable occlusion balloon extending out of a distal end tip of the catheter, which is received in the overtube passageway,
wherein after an insertion of the endoscope into a gastrointestinal tract portion the endoscope overtube is glided over the proximal end of the endoscope into the gastrointestinal tract portion and advanced so that the distal end portion gets close to distal end of the endoscope,
wherein after the diagnostic and therapeutic intervention the endoscope overtube is removable from the gastrointestinal tract portion and backward from the proximal end of the endoscope before a removing of the endoscope from the gastrointestinal tract portion, and
wherein the least one occlusion balloon is slidably moveable relative to the at least one endoscope overtube for selectively sealing a portion of the gastrointestinal tract portion for examination and therapeutic treatment.

12. The endoscope accessory of claim 11, wherein the positioning balloon is inflatable for creating a seal between the outer surface and a body cavity.

13. The endoscope accessory of claim 11, wherein the positioning balloon is inflatable for securing the endoscope into position.

14. The endoscope accessory of claim 11, wherein the washer comprises a soft material for creating a cushion for a seal between the overtube inner surface and the endoscope.

15. The endoscope accessory of claim 11, wherein the cuff is affixed to facilitate grasping and manipulation of the at least one elongated endoscope member for insertion and positioning inside a body cavity with the proximal end portion remaining outside the body cavity.

16. The endoscope accessory of claim 11, wherein the occlusion balloon can be inflated to create a seal inside a body cavity.

17. The endoscopy accessory of claim 11, wherein the occlusion balloon can be alternately inflated and deflated for independent positioning with a body cavity.

18. The endoscopy accessory of claim 11, further including a fluid conduit for infusing and emptying fluids and gases to and from a gastrointestinal tract portion for diagnostic and therapeutic intervention, wherein the fluid conduit is an additional overtube passageway for the introduction of air or fluids, suction of air or fluids, and the introduction of examination, diagnostic or therapeutic devices.

* * * * *